United States Patent [19]

McCormick

[11] Patent Number: 4,923,451
[45] Date of Patent: May 8, 1990

[54] SUCTION CONTROL CHAMBER HAVING A FILTER FOR USE IN CHEST DRAINAGE DEVICES

[75] Inventor: Michael A. McCormick, Rodman, N.Y.

[73] Assignee: Sherwood Medical Company, St. Louis, Mo.

[21] Appl. No.: 268,310

[22] Filed: Nov. 7, 1988

[51] Int. Cl.⁵ .............................................. A61M 1/00
[52] U.S. Cl. ................................. 604/321; 604/118
[58] Field of Search ............................. 604/317–321, 604/118, 119; 137/205

[56] References Cited

U.S. PATENT DOCUMENTS

| | | | |
|---|---|---|---|
| 3,545,440 | 12/1970 | Mishkin et al. | 128/276 |
| 3,782,497 | 1/1974 | Bidwell et al. | 181/33 |
| 4,258,824 | 3/1981 | Kurtz et al. | 181/233 |
| 4,439,190 | 3/1984 | Protzmann et al. | 604/319 |
| 4,601,715 | 7/1986 | Olson | 604/321 |
| 4,781,707 | 11/1988 | Boehringer et al. | 604/317 |

OTHER PUBLICATIONS

Sintercon by Advance Filtration Limited, date of publication unknown, Advanced Filtration Limited, Wietham North Wales, LL12 9YH.

*Primary Examiner*—Jerome L. Kruter
*Attorney, Agent, or Firm*—Andrew J. Beck; Montgomery W. Smith; Richard D. Allison

[57] ABSTRACT

A chest drainage device is provided for draining fluid and gases from the pleural cavity of a patient. The drainage device has three chambers; a collection chamber, a water seal chamber, and suction control chamber. The suction control chamber includes a first column which has an upper end adapted to be open to the atmosphere, and a second column, which has a substantially larger cross-sectional area than the first column. A filter member on the lower end of the first column disperses the atmospheric air into small diameter bubbles as it enters liquid present in the lower end of the second column. The present invention provides an improved means for muffling the sound of the atmospheric air as it bubbles through the liquid in the second column. Additionally, the present invention provides a means for increasing the accuracy of the vacuum pressure actually being applied to the pleural cavity of the patient as compared to the prescribed vacuum pressure.

9 Claims, 2 Drawing Sheets

SUCTION CONTROL CHAMBER HAVING A FILTER FOR USE IN CHEST DRAINAGE DEVICES

FIELD OF THE INVENTION

This invention relates to chest drainage units and more particularly to an improved suction control chamber having a porous filter therein to disperse atmospheric air as it enters a liquid present in the bottom of the suction control chamber.

BACKGROUND OF THE INVENTION

It is well known in treating pneumothorax and other conditions of the pleural cavity that it is essential to remove excess fluids, blood and gases, such as air, from the pleural space between the lung and the surrounding rib cage. Fluids may accumulate in the space between the lung and the chest wall as the result of surgery, wounds, or infections. In such situations, it is essential to the patient's survival that any excess fluids or gases be removed from the pleural cavity of the patient in order to maintain the lung in its expanded state.

The typical chest drainage device is generally known as a three-bottle system which includes a collection chamber, a water seal chamber and a suction control or manometer chamber. For example, if the vacuum source applies 35 cm $H_2O$ (source suction) and the desired vacuum pressure to the patient is 20 cm $H_2O$, liquid will be added to the suction control chamber until the liquid reaches a line indicating the desired 20 cm $H_2O$ vacuum pressure. Atmospheric air bubbles into the suction control chamber through the liquid to offset the excess vacuum pressure from the vacuum source to create a vacuum pressure of 20 cm $H_2O$ at the pleural cavity of the patient. During operation of these devices, atmospheric air is drawn into the suction control chamber through a first column and bubbles through the liquid in the bottom of the suction control chamber. The liquid level in the suction control chamber determines the actual amount of vacuum pressure being applied to the pleural cavity of the patient.

The chest drainage devices operate by drawing excess fluids and gases from the pleural cavity of the patient at the prescribed vacuum pressure. The excess fluid is collected in the collection chamber while the excess gases flow through the water seal chamber and into the vacuum source. The background and operation of chest drainage devices is discussed in more fully in U.S. Pat. No. 4,439,190, issued to Protzmann et al on Mar. 27, 1984 which is incorporated herein by reference.

One problem commonly associated with currently available chest drainage devices, is that as the atmospheric air is drawn into the bottom of the suction control chamber, the air bubbles violently through the liquid present in the bottom of the suction control chamber. The noise associated with this bubbling is frequently annoying to both the patient and the physician. Additionally, when this bubbling occurs at higher vacuum pressures, the bubbling may actually cause fluxuations in the amount of vacuum pressure being applied to the pleural cavity of the patient. Furthermore, under certain circumstances this violent bubbling at higher vacuum pressures may cause the liquid from the suction control chamber to be drawn into the vacuum source.

U.S. Pat. No. 3,782,497 issued to Bidwell et al on Jan. 1, 1974 discloses a sound muffling device which consists essentially of a plug-like member which is inserted into the top of the suction control chamber. This member is provided with a tortuous passageway therethrough in order to muffle the sound emanating from the device caused by the atmospheric air as it bubbles through the liquid in the suction control chamber.

Another approach is illustrated in U.S. Pat. No. 4,601,715 issued to Olson on July 22, 1986. This device consists of an elongate tube which is inserted into the first column of the suction control chamber. As the atmospheric air enters the suction control chamber, the elongate tube vibrates to dissipate the noise caused by the atmospheric air as it bubbles through the liquid in the suction control chamber.

Yet another approach is illustrated in U.S. Pat. No. 4,439,190 issued to Protzmann et al on Mar. 27, 1984. This device includes a foot member which is attached to the bottom of the first column in the suction control chamber. The foot member includes an enlarged end having a plurality of relatively small openings therein to cause the air bubbles to follow a circular path through the liquid in the suction control chamber.

Despite these and other chest drainage devices which are designed to decrease or muffle the noise caused by the atmospheric air as it bubbles through the suction control chamber, a need remains for an improved suction control chamber which will operate quietly and provide an accurate measurement of the amount of suction pressure actually being applied to the pleural cavity of the patient. Additionally, a need remains for a suction control chamber which will decrease the likelihood that liquid from the suction control chamber will be drawn into the vacuum source at higher vacuum pressures.

SUMMARY OF THE PRESENT INVENTION

It therefore an object of the present invention to provide an improved suction control chamber wherein the above-mentioned disadvantages are substantially obviated.

Another object of the present invention is to provide an improved suction control chamber which will decrease the amount of noise created during the normal operation of a chest drainage device.

Another object of the present invention is to provide an improved suction control chamber which will apply a consistent amount of vacuum pressure to the pleural cavity of the patient.

Another object of the present invention is to provide an improved suction control chamber which will decrease the likelihood that liquid will be drawn into the vacuum source from the suction control chamber.

A further object of the present invention is to provide an improved suction control chamber which may be readily adapted for use in nearly any chest drainage device.

In accordance with one form of the present invention, the improved suction control chamber is particularly designed for use in a three-bottle chest drainage device. Thus, the improved suction control chamber is designed for use in chest drainage devices having a collection chamber adapted to be in fluid communication with the patient's pleural cavity; a water seal chamber in flow communication with the collection chamber, and the suction control chamber adapted to be in in flow communication with the vacuum source and water seal chamber.

In the present invention, the suction control chamber is filled with a predetermined amount of water. The amount of water added to the suction control chamber determines the amount of suction to be applied to the pleural cavity patient. One end of the chest drainage device is the attached to the pleural cavity of the patient while the other end is attached to a vacuum source. The suction control chamber is generally of a two column design, wherein a first column includes an upper end adapted to be open to the atmosphere, and a second column, which has a substantially larger cross-sectional area than the first column. The bottom end of the first column opens into the bottom end of the second column so that the two columns are in flow communication with the atmosphere, the water seal column and the vacuum source. The vacuum applied by the vacuum source, to the suction control chamber is typically larger than the prescribed vacuum pressure. Therefore, there is unusually a substantial amount of bubbling as air from the first column is drawn into the suction control chamber to offset the difference between thevacuum pressure from the vacuum source and the desired amount of vacuum pressure being applied to the pleural cavity of the patient.

The suction control chamber of the present invention includes a porous filter located at the bottom end of the first column. This filter is designed to disperse the atmospheric air into small diameter bubbles as it passes from the first column into the liquid present in the bottom of the second column. By dispersing the atmospheric air into small diameter bubbles, the noise caused by the operation of this chest drainage device is decreased. Additionally, in this type of chest drainage device, the top surface of the liquid in the suction control chamber is used to indicate the vacuum pressure actually being applied to the pleural cavity of the patient during the operation of the chest drainage device. In the present invention, the top surface of the liquid remains relatively stable to provide for accurate monitoring of the vacuum pressure being applied to the pleural cavity of the patient. Finally, by maintaining a relatively stable liquid level in the suction control chamber, the likelihood that the liquid will be drawn into the vacuum source is decreased.

An advantage of the present invention is that it is relatively simple to manufacture and may be readily adapted for use in a variety of chest drainage devices.

A further advantage of the present invention is that it provides a simple means for reducing the noise caused by the atmospheric air as it bubbles through the liquid in the suction control chamber.

A further advantage of the present invention is that the top surface of the liquid of the suction control chamber more accurately reflects the actual amount of vacuum pressure being applied to the pleural cavity of the patient than in prior chest drainage devices.

A further advantage of the present invention is that the liquid in the suction control chamber is less likely to be drawn into the vacuum source when larger amounts of vacuum pressure are being applied to the pleural cavity of the patient.

DETAILED DESCRIPTION OF THE PREFERRED EMBODIMENT

Figure 1:
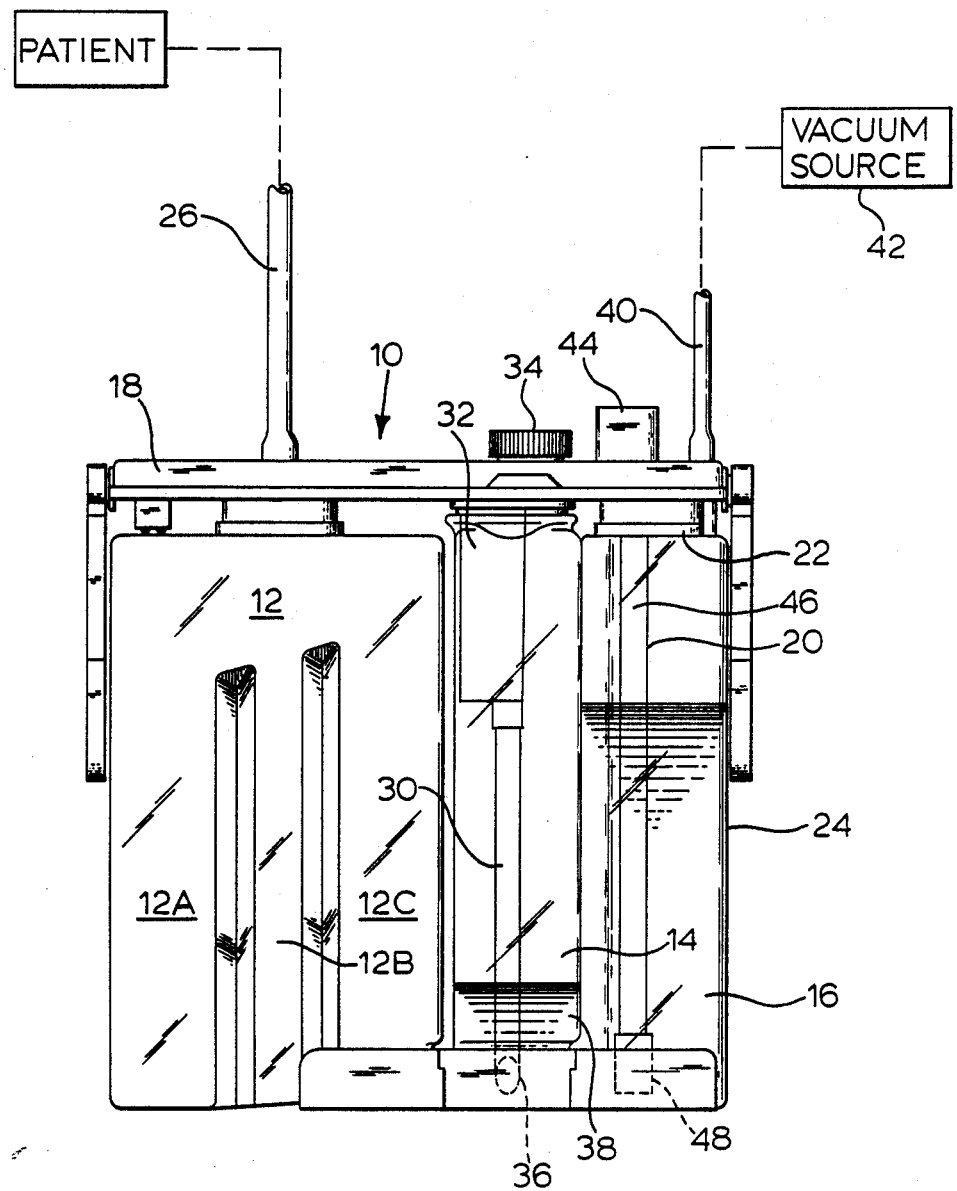
FIG. 1 is a side view of a chest drainage device in accordance with the present invention.
Figure 2:
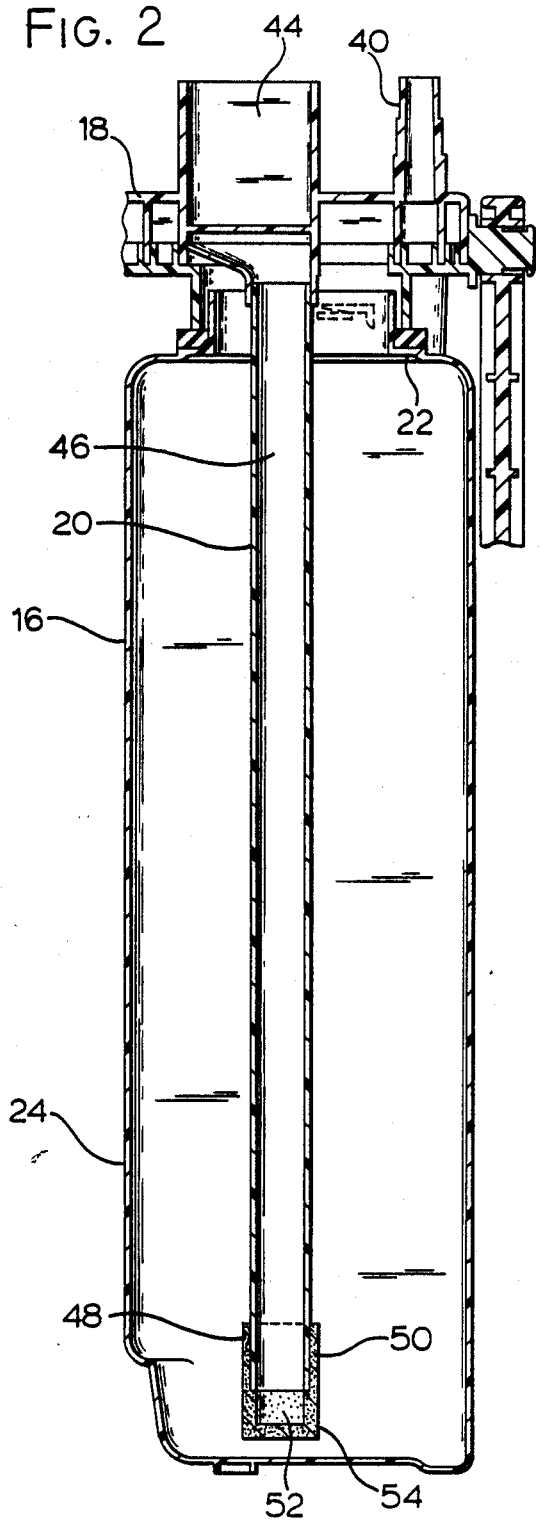
FIG. 2 is an enlarged cross-sectional view of the suction control chamber of the present invention.
Figure 3:
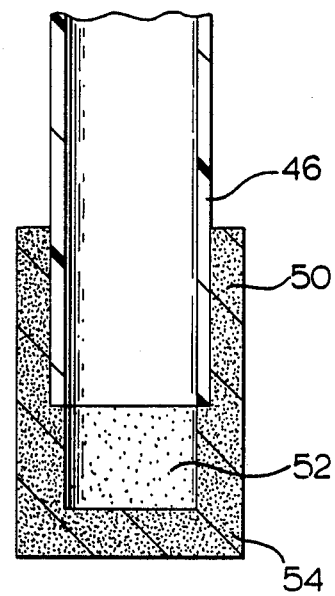
FIG. 3 is a cross-sectional view of the porous filter of the present invention.
Figure 4:
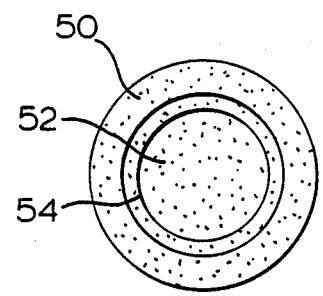
FIG. 4 is a top view of the porous filter of the present invention.

Referring now to FIG. 1 of the drawings, there is shown a drainage device 10 constructed in accordance with U.S. Pat. No. 4,439,190, herein incorporated by reference. It is to be understood that although the present invention is described with reference to the above-mentioned patent, the present invention is readily adaptable for use in a variety of chest drainage devices.

The chest drainage device 10 of the present invention consists generally of a collection chamber 12, a water seal chamber 14, a suction control chamber 16 and a manifold 18. In the preferred embodiment, the manifold 18 is attached to the top of the collection chamber 12 and the water seal chamber 14. The suction control chamber 16 is attached to the manifold 18 adjacent to the water seal chamber 14. The manifold 18 provides the desired flow communication between the collection chamber 12, the water seal chamber 14 and the suction control chamber 16, thus, eliminating the need for hoses, conduits and the like frequently used in a variety of other chest drainage devices.

In order to provide for the accurate measurement of the fluid collected from the pleural cavity of the patient, the collection chamaber 12 is provided with a pair of inner walls which divide the collection chamber 12 into three compartments 12a, 12b and 12c, respectively. The height of the first wall is less than the height of the second wall so that once the compartment designated as 12a is filled, the fluid will flow into the compartment designated as 12b. After compartment 12b is filled, fluid will spill over into a compartment designated as 12c. The external surface of each compartment has graduations thereon so that the attending physician or nurse can readily determine the amount of drainage collected from the pleural cavity of the patient.

The water seal chamber 14 includes a water seal column 30 and an upper baffle chamber 32. Liquid is poured into the water seal chamber 14 through a fill cap 34 until the liquid reaches the fill line indicated on the side of the water seal chamber 14. The volume of liquid placed in the water seal chamber 14 is designed to continuously cover the bottom opening 36 of the water seal column 30 during the typical operation of the drainage device 10. This liquid is known generally as the water seal and is referred herein as the water seal 38.

The suction control chamber 16 of the present invention functions similar to a standard U-shaped manometer chamber having a smaller diameter first column 20 and a larger diameter second column 24. In the preferred embodiment, the second column 24 consists of an elongate cylindrical design wherein the top end 22 is removably attached to the manifold 18. The first column 20 is enclosed within the second column 24 and consists of an elongate tube 46 which is in flow communication with a fill opening 44 on the manifold 18. The elongate tube 46 extends downwardly from the fill opening 44 into the bottom end of the second column 24. A filter member 48 encloses the bottom opening of the elongate tube 46.

In the present invention, the filter member 48 is adhesively bonded to the bottom end of the elongate tube 46. The filter member 48 is preferably constructed of a sintered high molecular weight homopolymer, such as a high density polyethylene. The filter member 48 is produced from a powder which is cryogenicaly ground, sized and sintered to produce a filter element having a preferred particle retention rate between 150 and 200 microns and a preferred permeability of about $600 \times 10^{-8} cm^2$. The particle retention rate is determined by immersing the filter member 48 in a wetting liquid and gradually increasing the air pressure applied to one side of the filter member 48. The amount of pressure exerted as the first bubble appears is a measure of the pore diameter which is then corrected by a factor of 0.2 for irregular pores. The permeability is directly related to the differential pressure applied up to the onset of turbulence and is a function of the pore size and the number of pores in the permeable area for a certain wall thickness. The filter member 48 consists of an upper section 50, an air chamber 52 and a filtration section 54. The upper section 50 holds the filter member 48 onto the bottom end of the tube 46. The air chamber 52 is formed immediately below the bottom opening of the tube 46 and assists in percolating the small diameter air bubbles through the filtration section 52.

The manifold 18 consists of a variety of openings and passageways to interconnect the collection chamber 12, the water seal chamber 14 and the suction control chamber 16. The manifold 18 also includes a plurality of restrictive passageways (not shown) therein to inhibit the flow of water between the various chambers while allowing various gases to be drawn therethrough from the pleural cavity of the patient. A vacuum hose 40 connects one end of the manifold 18 to the vacuum source 42. A drainage tube 26 connects the other end of the manifold 18 to the pleural cavity of the patient.

The chest drainage device 10 of the present invention functions similar to other chest drainage devices under normal operating conditions. Initially, a predetermined amount of liquid, such as water or normal saline, is added to the water seal chamber 14 through the fill cap 34 to create the water seal 38. Liquid is also added to the suction control chamber 16 through the fill opening 44 to a level corresponding to the prescribed patient vacuum pressure. Once the vacuum hose 40 is attached to the vacuum source 42 and the drainage tube 24 is attached to the pleural cavity of a patient, the process of drawing excess fluid from the patient's pleural cavity is begun. Normally, the vacuum pressure from the vacuum source 42 exceeds the prescribed patient vacuum pressure and atmospheric air is drawn into the suction control chamber 16 through the fill opening 44. The atmospheric air is draw the suction control chamber 16 at a rate equal to the difference between the vacuum pressure supplied by the vacuum source 42 and the prescribed patient vacuum pressure.

As the air is drawn through the elongate tube 46, the air is dispersed into small diameter air bubbles by the filtration section 52 of the filter member 48. The permeability and pore size of the filter member 48 creates a steady flow of small diameter air bubbles through the liquid in the second column. The steady flow rate of the small diameter air bubbles decreases the turbulence caused at the top surface of the liquid level and enables the physician or nurse to more accurately read the vacuum pressure actually being applied to the pleural cavity of the patient. Additionally, the liquid levels in certain prior chest drainage devices would bubble so violently that the liquid from the second column would be drawn into the vacuum source 42 and the vacuum pressure being applied to the pleural cavity of the patient would actually change as the device is operated over an extended period of time.

Comparative testing of chest drainage devices has been conducted using the filter member 48 of the present invention. Testing of prior art chest drainage devices indicates that the vacuum pressure actually applied to a patient may vary by as much as 5% from the desired vacuum pressure. For example, if the desired vacuum of a chest drainage device is 10 cm $H_2O$, the actual vacuum pressure being applied to the patient may be as high as 13 cm $H_2$: Additionally, if the desired vacuum pressure is 20 cm $H_2O$, the vacuum pressure actually being applied to the patient may be as high as 25 cm $H_2O$. Testing of chest drainage devices utilizing the filter member 48 of the present invention indicates that the variation between the desired vacuum pressure and the actual vacuum pressure being applied to the patient is less than 5%.

This differential between the prescribed vacuum pressure and actual vacuum pressure is important because the patient's diaphragm must overcome the vacuum pressure exerted by the chest drainage device in order for the patient to inhale while the chest drainage device is operating. Thus, increased accuracy is criticalin pediatric patients where the patient may be physically unable to overcome the increased vacuum pressure or in adults where the prescribed patient vacuum pressure may already be between 20 and 25 cm $H_2O$.

Additionally, the filter member 48 causes the air to flow through the second column 24 of the suction control chamber 16 at a steadier rate than in prior chest drainage devices where the rate of air flow is essentially unrestricted. The steadier rate of air flow decreases the bubbling noise caused by the operation of the chest drainage device 10 as compared to the bubbling noise caused by prior chest drainage devices. The steadier air flow also causes less disruption of the top surface of the liquid level to allow for the accurate reading of the vacuum pressure being applied to the pleural cavity of the patient.

What is claimed is:

1. A chest drainage device for removing liquids and gases from the pleural cavity of a patient comprising:
   a collection chamber in flow communication with the pleural cavity of a patient;
   a water seal chamber having a predetermined amount of liquid therein and wherein said water seal chamber is in flow communication with said collection chamber;
   a suction control chamber in flow communication with said water seal chamber and a vacuum source;
   said suction control chamber having first and second columns and a level of liquid in said second column;
   said first column having top and bottom ends and wherein said top end is in flow communication with the atmosphere and wherein said bottom end is positioned in the level of liquid in said second column;
   a filter means on the bottom end of and externally surrounding the bottom end said first column in flow communication with said first column and the atmosphere wherein said filter means includes an air chamber therein for dispersing atmospheric air therefrom as the atmospheric air is drawn into said second column of said suction control chamber; and said second column having a top end in flow communication with said water seal chamber and a vacuum source and a bottom end in flow communication with said filter means and wherein atmospheric air is drawn through said filter means into the liquid in said suction control chamber.

2. The chest drainage device of claim 1, wherein the filter means is porous to allow atmospheric air to pass through the pores of said filter means.

3. The chest drainage device of claim 2, wherein the filter means has a pore size between approximately 150 and 200 microns.

4. The chest drainage device of claim 2, wherein the filter means has a permeability of approximately $600 \times 10^{-8} cm^2$.

5. The chest drainage device of claim 1, wherein the filter means is constructed of a sintered high density homopolymer.

6. The chest drainage device of claim 1, wherein the filter means is constructed of a porous high density polyethylene.

7. A chest drainage device for removing liquids and fluid from the pleural cavity of a patient comprising:
 a collection chamber in flow communication with the pleural cavity of a patient;
 a water seal chamber having a predetermined amount of liquid therein and wherein said water seal chamber is in flow communiction with said collection chamber;
 a suction control chamber in flow communication with said water seal chamber and a vacuum source;
 said suction control chamber having a first and second column therein and a variable level of liquid therein;
 said first column having top and bottom ends and wherein said top end is in flow communication with the atmosphere and wherein the bottom end is in flow communication with the second column;
 a filter means is affixed to and encloses the bottom end of said first column and wherein said filter means includes porous sidewalls and a porous bottom wall to form an air chamber therein adjacent to the bottom end of said first column to disperse the atmospheric air through the porous sidewalls and into small diameter bubbles as it is drawn through the first column into the liquid in the second column; and
 said second column having a top end in flow communication with said water seal chamber and vacuum source and a bottom end in flow communication with said first column.

8. The chest drainage device of claim 7, wherein the filter means is a porous filter having a pore size between approximately 150 and 200 microns.

9. The chest drainage device of claim 7, wherein the filter means is constructed of a porous high density homopolymer and includes an an upper section which engages and surrounds the bottom end of said first column and a filter surface formed by the sidewalls and bottom wall of said filter means to disperse atmospheric air into small diameter air bubbles.

* * * * *